United States Patent
Price

(10) Patent No.: US 6,740,683 B2
(45) Date of Patent: May 25, 2004

(54) CHEMICALS FROM SYNTHESIS GAS

(75) Inventor: Julian Graham Price, Vanderbijlpark (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 10/153,079

(22) Filed: May 22, 2002

(65) Prior Publication Data

US 2003/0018086 A1 Jan. 23, 2003

Related U.S. Application Data

(60) Provisional application No. 60/293,075, filed on May 23, 2001.

(30) Foreign Application Priority Data

May 23, 2001 (ZA) .......................................... 2001/4213

(51) Int. Cl.⁷ ................................................ C07C 27/00
(52) U.S. Cl. ....................... 518/719; 518/700; 518/702; 518/713; 518/715; 518/717
(58) Field of Search ................................. 518/700, 702, 518/713, 715, 717, 719

(56) References Cited

U.S. PATENT DOCUMENTS 6,310,108 B1 * 10/2001 Bonneau et al. ............. 518/700
6,479,557 B1 * 11/2002 Lange et al. ................. 518/706

* cited by examiner

Primary Examiner—J. Parsa
(74) Attorney, Agent, or Firm—Brinks Hofer Gilson & Lione

(57) ABSTRACT

This invention relates to a process for selectively producing linear alcohols, olefins and paraffins from hydrogen-poor carbonaceous fuels such as coal, petroleum coke, or heavy residue oil in a Fischer-Tropsch reactor. The process includes producing synthesis gas, modifying the ratio of hydrogen to carbon monoxide in the synthesis gas to a ratio that is at or above the overall $H_2/CO$ usage ratio in the reactor, but less than 2. The modified synthesis gas is combined with a recycled vapor product from the reactor to provide combined synthesis gas having a hydrogen/carbon monoxide ratio of greater than 2 and less than 3. The combined synthesis gas is introduced into the reactor, and the hydrogen and carbon monoxide in the combined synthesis gas is reacted with an iron-based catalyst under Fischer-Tropsch conditions.

11 Claims, 1 Drawing Sheet

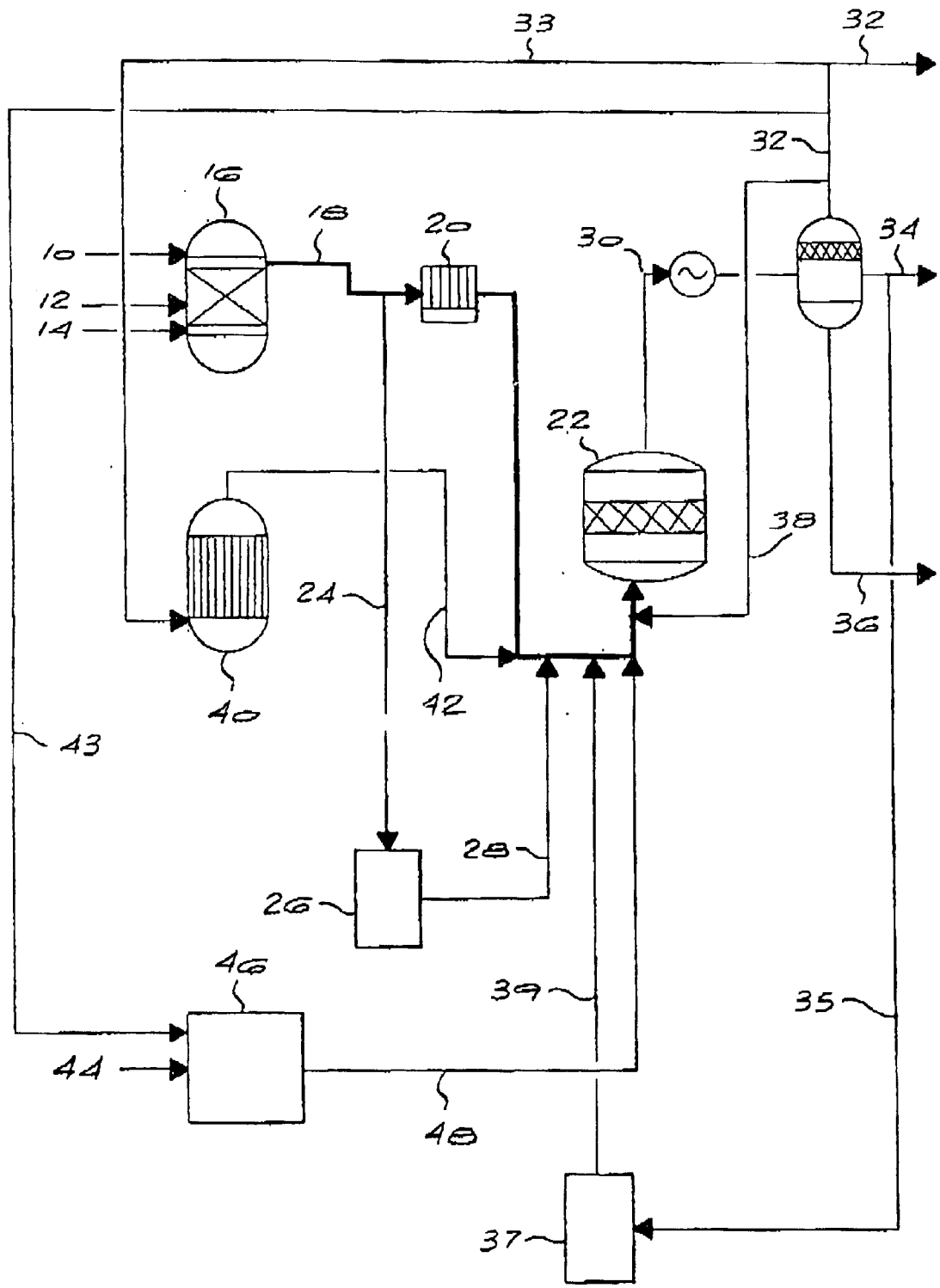

CHEMICALS FROM SYNTHESIS GAS

This application claims the benefit under 35 U.S.C. §119(e) of Provisional U.S. patent application Serial No. 60/293,075, filed May 23, 2001.

BACKGROUND OF THE INVENTION

The conversion of synthesis gas to hydrocarbons is well known in the art, and the use of numerous catalytic processes have been suggested for optimal operation thereof. See for example Anderson R "The Fischer Tropsch synthesis", academic press, New York, 1984.

Many technologies exist to convert coal or other solid carbonaceous fuels to synthesis gas. The synthesis gas so produced consists predominantly of $H_2$, CO, $CO_2$ and $CH_4$. The conversion of coal or other solid carbonaceous fuels to synthesis gas is also known as "gasification" and typically is carried out in the presence of steam and oxygen in a gasifier such as a BGC-Lurgi slagging gasifier or a Texaco gasifier.

Synthesis gas so produced is reacted under Fischer-Tropsch conditions to produce gaseous and liquid hydrocarbons and oxygenates, containing amongst others, paraffins, olefins, alcohols and aromatics, with a variety of carbon chain length ranges and isomers which, in general, follow the well-known Anderson-Schultz-Flory distribution. For example, iron based catalysts are known for producing C2–C20 olefins, wherein the olefins comprise 60–70% by weight of the hydrocarbon products. Disclosures in the art, aimed at developing such catalyst systems and/or processes include, amongst others, the following patents: U.S. Pat. Nos. 4,604,375, 4,621,102, 4,618,597, 5,100,856, 5,118, 715, 5,162,284, 5,185,378, GB 2 151 500A, and EP 0 446 035 A2.

The Fischer-Tropsch reaction is comprised of a series of polymerization reactions that can be represented by the generic chemical equations:

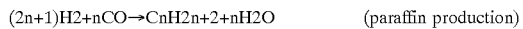

(2n+1)H2+nCO→CnH2n+2+nH2O     (paraffin production)

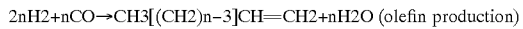

2nH2+nCO→CH3[(CH2)n-3]CH=CH2+nH2O (olefin production)

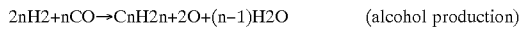

2nH2+nCO→CnH2n+2O+(n-1)H2O     (alcohol production)

In addition, some catalysts that are active for the Fischer Tropsch reaction are also active for the water gas shift (WGS) reaction shown below. Fe based catalysts are notable in this regard.

CO+H2O⇌CO2+H2     (water gas shift)

There are also a number of side reactions in which ketones, aldehydes, organic acids, branched hydrocarbons and cyclic compounds are formed. These compounds represent generally undesirable products, and efforts should be made to minimize production thereof A homologous series of predominantly straight chain hydrocarbons and alcohols with carbon number from 1 to greater than 100 may be formed, although substantial level of chain branching, particularly methyl branching is common for many catalyst systems.

Fe and Co based catalysts are of industrial interest. As indicated, iron based catalysts, as opposed to cobalt based catalysts are well known to be active for the water gas shift reaction (WGSR) and are thus able to convert synthesis gas with a low H2/CO ratio into liquid hydrocarbon products and CO2. This situation prevails when a hydrogen poor carbonaceous feedstock such as coal is gasified to synthesis gas.

It is an object of the invention to provide an improved process for producing longer chain alcohols and olefins from a raw carbonaceous feedstock which yields synthesis gas with a low H2/CO ratio, such as coal.

SUMMARY OF THE INVENTION

According to the invention there is provided a process for selectively producing linear alcohols, olefins and paraffins in a Fischer-Tropsch reactor, the process including:

producing synthesis gas containing hydrogen and carbon monoxide from a carbonaceous fuel;

modifying the ratio of hydrogen to carbon monoxide in the synthesis gas to a ratio that is at or above the overall hydrogen/carbon monoxide usage ratio in the reactor, but less than 2, typically between 1.2 and 2;

combining the modified synthesis gas with a recycled vapor product from the reactor to provide combined synthesis gas having a hydrogen/carbon monoxide ratio of greater than 2 and less than 3;

introducing the combined synthesis gas into the reactor;

reacting the hydrogen and carbon monoxide in the combined synthesis gas with an iron-based catalyst under Fischer-Tropsch conditions within the reactor; and recovering linear alcohols, olefins and paraffins produced in the reactor.

The overall hydrogen/carbon monoxide usage ratio is a combination of the quantity of hydrogen consumed per mole of carbon monoxide in the Fischer-Tropsch reaction and the carbon monoxide converted to carbon dioxide and hydrogen by the water gas shift reaction.

The carbonaceous fuel is typically a hydrogen-poor carbonaceous fuel such as coal, petroleum coke or heavy residual oil.

The molar ratio of hydrogen to carbon monoxide in the synthesis gas may be modified by combining the synthesis gas with a second stream of gas containing hydrogen and carbon monoxide at a high molar ratio, typically of from 2 to 4.

The second stream of gas may be produced by:

a) passing synthesis gas through a water-gas shift reactor containing a catalyst that is active for a water-gas shift reaction but which is not active for hydrocarbon synthesis;

b) obtaining a paraffinic liquid hydrocarbon product from the reactor, passing the paraffinic liquid through a reforming reactor to convert the liquid to a reformed gas, and combining the reformed gas with the synthesis gas introduced in to the reactor;

c) utilizing a natural gas or refinery off gas stream or vapor stream from the Fischer-Tropsch reactor as feed to a steam reformer; or d) a combination of any of the above methods a) to c).

A preferred iron-based catalyst for use in the above process is typically one in which the main iron phase is ferrihydrite and which includes Mn, Zn, Cu and K structural and chemical promoters.

For example, the iron based catalyst may, by mass, comprise:

35%–60% Fe, preferably 45%–60% Fe

0%–15% Mn, preferably 7%–15% Mn

3%–10% Zn, preferably 3%–7% Zn 0.5%–2% Cu, preferably 0.5%–1% Cu; and 0.5%–2% $K_2O$, preferably 0.5%–1% $K_2O$.

When bound with silica, the iron-based catalyst typically contains, by mass of the composition, 1%–30% silica.

BRIEF DESCRIPTION OF THE DRAWING

The invention will now be described in more detail, by way of example only, with reference to the accompanying drawing which shows a schematic diagram of a process according to the invention.

DETAILED DESCRIPTION OF THE INVENTION

This invention relates to a process for selectively producing linear alcohols, olefins and paraffins by producing synthesis gas containing hydrogen and carbon monoxide from hydrogen poor carbonaceous fuel (feedstock), modifying the molar ratio of hydrogen to carbon monoxide in the synthesis gas and converting the hydrogen and carbon monoxide in the synthesis gas under Fischer-Tropsch conditions (at pressures of 20 to 100 bar ($2 \times 10^6$ to $10 \times 10^6$ Pa) and low temperatures of 200 to 260° C.) in the presence of an iron-based catalyst composition, to paraffins, olefins and, more especially, to alcohols in significant yields, up to and including detergent alcohols. The composition of the product stream contains greater than 50 weight percent of combined alcohols and olefins, the remainder consisting of predominantly paraffins. In particular, the product stream contains greater than 20 weight percent alcohols.

Catalyst compositions according to preferred embodiments of the invention are iron based and include one or more promoters selected from Mn, Cr, Zn, Mg, Cu, Ru, Pd, Rh and/or an alkali or alkaline earth metal such as K. The iron-based catalyst compositions are preferably bound to a refractory oxide such as silica, alumina or silica-alumina. Typical iron based catalyst compositions are described in more detail in International patent publication no. WO 01/89689, which is incorporated herein by reference.

By "iron-based" is meant that Fe makes up at least 30% (by mass) of the composition. A particularly preferred "iron-based" catalyst is one in which the main iron phase is ferrihydrite. The term "the main iron phase is ferrihydrite" means that at least 75% of the iron phase is ferrihydrite, as determined by X-ray diffraction using Co K alpha radiation. The preferred catalyst compositions exhibit hyperfine interaction parameters similar to those of ferrihydrite, as determined by Mossbauer absorption spectroscopy (MAS).

The iron-based catalyst composition optionally also comprises a structural promoter selected from Mn, Cr or a mixture thereof and a chemical promoter or promoters selected from Zn, Mg, Cu, Ru, Pd, Rh and/or an alkali or alkaline earth metal such as K. A "structural promoter" is a chemical species/element that helps to stabilize the ferrihydrite phase of the catalyst. A "chemical promoter" is a chemical species/element that alters the product selectivity and activity of a catalyst.

Advantageously, the iron-based catalyst composition has a surface area from 50 to 200 $m^2/g$, typically from 100 to 200 $m^2/g$, as determined by the BET surface area measurement technique.

A preferred iron-based catalyst composition includes Cu and K and optionally Mn and Zn promoters and is best bound with a refractory oxide which may be selected from silica, alumina or silica-alumina, preferably silica.

For example, the iron-based catalyst composition may, by mass of the composition, comprise:

35%–60% Fe, preferably 45%–60% Fe
0%–15% Mn, preferably 7%–15% Mn
3%–10% Zn, preferably 3%–7% Zn
0.5%–2% Cu, preferably 0.5%–1% Cu; and
0.5%–2% $K_2O$, preferably 0.5%–1% $K_2O$.

When bound with silica, the iron-based catalyst composition typically contains, by mass of the composition, 1%–30% silica.

The iron-based catalyst composition may further comprise other materials such as other promoters, activators, spacers, carriers, diluents and supports. These other materials may include zeolites, pulverized borosilicate glass, pulverized quarts, kieselguhr, silicon carbide, Group II to VII oxides and rare earth oxides including but not limited to MgO, $Al_2O_3$, $TiO_2$, $ThO_2$, $Cr_2O_3$, MnO, $ZrO_2$, $La_2O_3$ and $CeO_2$.

Referring to the drawing, in an embodiment of the invention hydrogen poor carbonaceous fuel 10, together with oxygen 12 and possibly steam 14, is fed into a suitable gasifier 16 to produce synthesis gas which consists predominantly of $CH_4$, CO, $H_2$, $CO_2$, $N_2$ and low molecular weight hydrocarbons. The gasifier 16 is typically a high efficiency gasifier such as the BGC-Lurgi slagging gasifier. The synthesis gas 18 thus formed is sent to a treatment unit 20 that removes impurities such as $H_2S$, COS and $NH_3$. The treatment may also optionally remove $CO_2$.

The carbonaceous fuel 10 may be solid (such as coal or petroleum coke), or liquid (such as heavy residue oil arising from conventional oil refining operations for example vacuum residue or visbreaker residue). These carbonaceous fuels inherently provide a hydrogen poor synthesis gas i.e. a $H_2$/CO molar ratio which is below 2.

From the treatment unit 20, the synthesis gas 18 is introduced to a Fischer-Tropsch reactor 22, after having the molar ratio of the hydrogen to carbon monoxide modified, as described below.

The Fischer-Tropsch synthesis process according to an embodiment of the invention is carried out in a slurry bubble column reactor containing a crude synthetic paraffin or wax liquid with a carbon chain length varying from $C_{10}$ to $C_{120}$, such as the wax obtained from a slurry phase reactor process, using either Fe or Co based catalysts. Optionally the reactor may have a means of internal agitation. This is preferably in the form of one or more draft tubes situated inside or, less preferably, outside the reactor. Advantageously, these draft tubes should be designed to induce circulation of the slurry. An iron-based catalyst composition as described above is then suspended in the slurry medium, the catalyst loading ranging between 10 and 40% by weight of the slurry. The catalyst particles are between 20 and 300 microns in diameter, preferably between 50 and 200 microns. The slurry is agitated and conditioned by causing pure hydrogen or a hydrogen rich mixture to flow continuously through the medium for approximately 20 hours (in practice, the conditioning may take place in a separate reactor, and the conditioned catalyst transferred to the Fischer-Tropsch reactor). Thereafter, synthesis gas is caused to flow continuously through the conditioned slurry.

Throughout the conditioning process and synthesis process, the reactor is operated at a temperature between 200 and 300° C.; preferably between 220 and 250° C., and pressure between 10 and 100 bar ($1 \times 10^6$ and $10 \times 10^6$ Pa) preferably between 20 and 80 bar ($2 \times 10^8$ and $8 \times 10^6$ Pa).

As mentioned in the Summary of the Invention, during the synthesis process a series of polymerization reactions take place, to form paraffins, olefins and alcohols which exit the reactor 22 as a liquid or an overhead product. In accordance with normal practice, an overhead vapor product 30 from the reactor 22, exits near the top of the reactor 22. The vapor 30 is cooled and separated into a vapor fraction 32, liquid hydrocarbon fraction 34 and an aqueous fraction 36. The vapor fraction 32 consists of unconverted CO and $H_2$ as well as low molecular weight hydrocarbons and $CO_2$. A portion of this vapor fraction 32, which typically has a $H_2/CO$ ratio of 2 to 4, is recycled in a stream 38 into the reactor 22.

In addition to the synthesis reaction, the iron-based catalyst is active for the water-gas shift reaction under the abovementioned Fischer-Tropsch conditions. This is advantageous as the iron-based catalyst replenishes $H_2$ in the reactor via the water-gas shift reaction thereby increasing the $H_2/CO$ ratio for the synthesis reaction. A cobalt-based catalyst on the other hand is not active for the water-gas shift reaction and does not have this advantage.

It has been found that the optimal molar ratio of $H_2/CO$ in the synthesis gas introduced to the reactor will depend on the relative activity of the iron-based catalyst for the water-gas shift reaction and the Fischer-Tropsch reaction and will be different depending on the particular catalyst formulation and synthesis conditions. It has further been found that the ratio of the activities of the water-gas shift reaction and the Fischer-Tropsch reaction determines the usage ratio for the catalyst. The Fischer-Tropsch usage ratio is defined as the number of moles $H_2$ used per mole of CO for the production of hydrocarbon products. The overall $H_2/CO$ usage ratio is thus the ratio of $H_2$ to CO used within the reactor and is lower than the Fischer-Tropsch usage ratio due to the effect of the water-gas shift reaction.

In order to produce the required linear alcohols, olefins and paraffins, it is important for the synthesis gas to enter the reactor with a high $H_2/CO$ ratio of above 2, but less than 3. Even with the recycle stream 38, it is difficult to reach such a high ratio with hydrogen poor carbonaceous feedstock and it has been found that it is necessary to modify the synthesis gas, prior to the point at which it is combined with the recycled vapor phase products. In particular, it has been found that the synthesis gas should be modified to a $H_2/CO$ molar ratio at, or above, the overall usage ratio but less than 2. Advantageously, the synthesis gas should be modified to a $H_2/CO$ ratio slightly above the $H_2/CO$ overall usage ratio of the reactor, and in the range of between 1.2 and 2.

The following methods may be used for modifying the $H_2/CO$ ratio of the synthesis gas:

a) Part of the synthesis gas 18 that is produced in the gasifier 16 is passed via a stream 24 through a water-gas shift reactor 26 containing a catalyst that is active for the water-gas shift reaction but which is not active for hydrocarbon synthesis, thereby obtaining a stream of gas 28 containing a modified $H_2/CO$ ratio. The catalyst may contain metals such as copper, zinc and aluminum. The stream of gas 28 from this water-gas shift reactor 26 is then combined with the synthesis gas stream 18 from the carbonaceous fuel conversion process and introduced to the Fischer-Tropsch reactor 22.

b) The synthesis gas 18 introduced to the reactor 22 is modified by recycling paraffinic liquid hydrocarbon product from the liquid hydrocarbon fraction 34 of the Fischer-Tropsch reactor 22 via a stream 35, passing the paraffinic liquid hydrocarbon product through a reforming reactor 37 which comprises a suitable reforming catalyst, then, via a stream 39, combining the gas thus formed with the synthesis gas 18 which is added to the reactor 22. The paraffinic hydrocarbon product will generally consist of $C_3$ to $C_{15}$ paraffinic hydrocarbons.

c) Part of the vapor product 32 from the synthesis reactor is directed via a stream 33 to a steam reformer 40, part or all of the $CO_2$ is removed and the gas stream may optionally be passed through a water-gas shift reactor and then via a stream 42 added to the synthesis gas 18 which is introduced into the reactor 22.

d) Natural or refinery gas 44 from a conventional refinery or a portion of the vapor product 32 from the reactor 22 fed via stream 43 may be used as a feed to a reforming unit 46 and the gas so produced, via a stream 48 added to the synthesis gas 18 which is introduced to the Fischer-Tropsch reactor 22. The reforming unit 46 may be a steam reformer, catalytic auto thermal reformer or any combination thereof or any other means of converting natural gas or naphtha into synthesis gas with a $H_2/CO$ ratio greater than the syngas $H_2/CO$ ratio required for the process herein described.

e) The synthesis gas may be modified by using a combination of steps a) to d) mentioned above.

The process of the present invention produces significant yields of alcohols at reactor pressure values of between 20 to 80 bar ($2 \times 10^6$ and $8 \times 10^6$ Pa). The results have surprisingly shown that under the pressure and temperature synthesis conditions according to invention, the total yield of alcohols in the may be in excess of 30% by mass.

In addition there are two other significant co-products of the process that are formed together with the alcohol stream, viz. the ($C_2$—greater than $C_{30}$) n-paraffins which are also characterized by greater than about 85% linearity, and the alpha-olefins in the range of C2 to greater than C30.

In fact, the catalyst and process exhibits almost clean-cut selectivity towards the olefins, paraffins and alcohols which are fairly easy to separate using known processes. Prior art processes tend to produce a large product distribution with hydrocarbons, including aromatics that are difficult to separate. The catalyst and process of the present invention produces almost no aromatics, unlike, for example, SASOL's Synthol fused iron catalyst which operates at higher temperatures and produces aromatics in significant yields. The Synthol process produces olefins, but it also yields skeletal isomers and aromatics, which generally translates to an increase in the separation costs. The process of the present invention produces negligible amounts of isomers (approx. 10%), and only traces of aromatics are observed in the product stream. Therefore, the decrease in the capital cost for the down-stream separation and purification units is significant.

The catalyst of the invention can also be used in a fluidized bed reactor or a fixed bed reactor.

The products of the present invention, either in pure or mixed form, have a number of beneficial uses. The low molecular weight olefins have uses as co-monomers in the manufacture of polyolefins or may be oxidized or oligomerized. High molecular weight olefins may be used in hydroformulation processes for the production of alcohols in the plasticizer and detergent ranges. Alternatively, they may be used to produce linear alkyl benzene, halogenated olefins or synthetic lubricants. The aqueous stream contains substantial quantities of low molecular weight alcohols that can be easily purified. These have application principally as solvents and as fuel additives. The longer chain alcohols may be sulphonated or converted into alkoxylates which find utility as detergents. Amines may also be produced by dehydration of the alcohols and the reaction with ammonia. The amines may be used as surfactants. This list of uses of products of the invention is not exhaustive and only serves as an example on the usefulness of the process. Numerous other processes may be proposed utilizing feedstocks derived from the process of the current invention.

What is claimed is:

1. A process for selectively producing linear alcohols, olefins and paraffins in a Fischer-Tropsch reactor, the process including:
   producing synthesis gas containing hydrogen and carbon monoxide from a carbonaceous fuel;
   modifying the ratio of hydrogen to carbon monoxide in the synthesis gas to a ratio that is at or above the overall hydrogen/carbon monoxide usage ratio in the reactor, but less than 2;
   combining the modified synthesis gas with a recycled vapor product from the reactor to provide combined synthesis gas having a hydrogen/carbon monoxide ratio of greater than 2 and less than 3;
   introducing the combined synthesis gas into a reactor;
   reacting the hydrogen and carbon monoxide in the combined synthesis gas with an iron-based catalyst under Fischer-Tropsch conditions within the reactor; and
   recovering linear alcohols, olefins and paraffins produced in the reactor.

2. A process according to claim 1, wherein the ratio of hydrogen to carbon monoxide in the synthesis gas is modified to between 1.2 and 2.

3. A process according to claim 1, wherein the carbonaceous fuel is a hydrogen-poor carbonaceous fuel.

4. A process according to claim 3, wherein the carbonaceous fuel is coal, petroleum coke or heavy residual oil.

5. A process according to claim 1, wherein the molar ratio of hydrogen to carbon monoxide in the synthesis gas is modified by combining the synthesis gas with a second stream of gas containing hydrogen and carbon monoxide at a higher molar ratio.

6. A process according to claim 5 wherein the second gas stream is produced by:
   a) passing synthesis gas through a water-gas shift reactor containing a catalyst that is active for a water-gas shift reaction but which is not active for hydrocarbon synthesis;
   b) recycling unconverted synthesis gas from an outlet of the reactor;
   c) obtaining a paraffinic liquid hydrocarbon product from the reactor, passing the paraffinic liquid through a reforming reactor to convert the liquid to a reformed gas, and combining the reformed gas with the synthesis gas introduced in to the reactor;
   d) utilizing a natural gas, refinery off gas stream or vapor product from the synthesis reactor as feed to a steam reformer; or
   e) a combination of any of the above methods a) to d).

7. A process according to claim 1 wherein the iron-based catalyst includes Mn, Zn, Cu and K promoters.

8. A process according to claim 7 wherein the iron-based catalyst comprises, by mass:
   35%–60% Fe;
   0%–15% Mn;
   3%–10% Zn;
   0.5%–2% Cu; and
   0.5%–2% $K_2O$.

9. A process according to claim 8 wherein the iron-based catalyst comprises, by mass:
   45%–60% Fe;
   7%–15% Mn;
   3%–7% Zn;
   0.5%–1% Cu; and
   0.5%–1% $K_2O$.

10. A process according to claim 9 wherein the iron-based catalyst contains, by mass, 1%–30% silica.

11. A process according to claim 1 wherein the main iron phase of the catalyst is ferrihydrite.

* * * * *